United States Patent [19]
Squires et al.

[11] Patent Number: 5,985,650
[45] Date of Patent: Nov. 16, 1999

[54] METHOD OF DESULFURIZATION OF FOSSIL FUEL WITH FLAVOPROTEIN

[75] Inventors: Charles H. Squires; Wan Ji; Lei Xi, all of The Woodlands; Beatrice C. Ortego, Spring; Olga S. Pogrebinsky, Houston; Kevin A. Gray; John D. Childs, both of The Woodlands, all of Tex.

[73] Assignee: Energy BioSystems Corporation, The Woodlands, Tex.

[21] Appl. No.: 09/025,527

[22] Filed: Feb. 18, 1998

Related U.S. Application Data

[63] Continuation of application No. 08/351,754, Dec. 8, 1994.
[51] Int. Cl.$^6$ .............. C12N 9/02; C10G 32/00
[52] U.S. Cl. ............ 435/282; 435/189; 435/281
[58] Field of Search .................. 435/282, 281, 435/189

[56] References Cited

U.S. PATENT DOCUMENTS

| | | | |
|---|---|---|---|
| 5,356,801 | 10/1994 | Rambosek et al. | 435/195 |
| 5,733,773 | 3/1998 | Squires et al. | 435/252.3 |

OTHER PUBLICATIONS

Denome, Sylvia A. et al., "Characterization of the Desulfurization Genes from Rhodococcus sp. Strain IGTS8," *Journal of Bacteriology* 176 (21) :6707–6716 (1994).

Lei, Benfang et al., "*Vibrio harveyi* NADPH–Flavin Oxidoreductase: Cloning, Sequencing and Overexpression of the Gene and Purification and Characterization of the Cloned Enzyme," *Journal of Bacteriology* 176 (12):3552–3558 (1994).

Ohshiro, Takashi et al., "Enzymatic desulfurization of dibenzothiophene by a cell–free system of *Rhodococcus erthropolis* D–1," *FEMS Microbiology letters* 118:341–344 (1994).

Ohshiro, Takashi et al., "Involvement of Flavin Coenzyme in Dibenzothiophene Degrading Enzyme System from *Rhodococcus erythropolis* D–1," *Biosci. Biotech. Biochem.*, 59(7): 1349–1351 (1995).

Piddington, Christopher S. et al., "Sequence and Molecular Characterization of DNA Region Encoding the Dibenzothiophen Desulfurization Operon of Rhodococcus sp. Strain IGTS8," *Applied and Environmental Microbiology*, 61 (2):468–475 (1995).

Nagy, István et al., "Characterization of the Rhodococcus sp. NI86/21 gene encoding alcohol: N,N'–dimethyl–4–nitrosoaniline oxidoreductase inducible by atrazine and thiocarbamate herbicides," *Arch Microbiol.*, 163:439–446 (1995).

*Primary Examiner*—Robert A. Wax
*Assistant Examiner*—Einar Stole
*Attorney, Agent, or Firm*—Hamilton, Brook, Smith & Reynolds, P.C.

[57] ABSTRACT

The invention relates to the discovery that the rate of reaction of the desulfurization of fossil fuels is enhanced by the addition of a flavoprotein to the biocatalyst. The invention is drawn to a method for enhancing the rate of desulfurizing a fossil fuel containing organic sulfur compounds, comprising the steps of:

a) contacting the fossil fuel with an aqueous phase containing a biocatalyst capable of cleaving carbon-sulfur bonds and a rate-enhancing amount of a flavoprotein, thereby forming a fossil fuel and aqueous phase mixture;

b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase. The invention also relates to a recombinant microorganism containing one or more recombinant DNA molecules which encode a biocatalyst capable of desulfurizing a fossil fuel containing organic sulfur molecules and which encode a flavoprotein. The invention also relates to a composition comprising (a) a biocatalyst capable of desulfurizing a fossil fuel containing organic sulfur molecules and (b) a flavoprotein.

17 Claims, 6 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 77 base pairs
      (B) TYPE: nucleic acid
      (C) STRANDEDNESS: double
      (D) TOPOLOGY: linear    (ii) MOLECULE TYPE: DNA (genomic)

(ix) FEATURE:
      (A) NAME/KEY: CDS
      (B) LOCATION: 31..54

(xi) SEQUENCE DESCRIPTION: SEQ ID NO:1:

```
AATTCAGATC TGATCGAGGA GGATGATTAA ATG ACT CAA CAA CGA CAA ATG CAT        54
                                Met Thr Gln Gln Arg Gln Met His
                                 1               5

CTGATACGTA CGACTAGTAA GCT                                                77
```

(2) INFORMATION FOR SEQ ID NO:2:

(i) SEQUENCE CHARACTERISTICS:
      (A) LENGTH: 8 amino acids
      (B) TYPE: amino acid
      (D) TOPOLOGY: linear    (ii) MOLECULE TYPE: protein    (xi) SEQUENCE DESCRIPTION: SEQ ID NO:2:

```
Met Thr Gln Gln Arg Gln Met His
 1               5
```

METHOD OF DESULFURIZATION OF FOSSIL FUEL WITH FLAVOPROTEIN

RELATED APPLICATION

This application is a continuation of U.S. application Ser. No. 08/351,754, filed Dec. 8, 1994, the entire teachings of which is incorporated herein by reference.

BACKGROUND OF THE INVENTION

The microbial desulfurization of fossil fuels has been an area of active investigation for over fifty years. The object of these investigations has been to develop biotechnology based methods for the pre-combustion removal of sulfur from fossil fuels, such as coal, crude oil and petroleum distillates. The driving forces for the development of desulfurization methods are the increasing levels of sulfur in fossil fuel and the increasingly stringent regulation of sulfur emissions. Monticello et al., "Practical Considerations in Biodesulfurization of Petroleum," IGT's 3d Intl. Symp. on Gas, Oil, Coal and Env. Biotech., (Dec. 3–5, 1990) New Orleans, La.

Many biocatalysts and processes have been developed to desulfurize fossil fuels, including those described in U.S. Pat. Nos. 5,356,801, 5,358,870, 5,356,813, 5,198,341, 5,132,219, 5,344,778, 5,104,801 and 5,002,888, incorporated herein by reference. Economic analyses indicate that one limitation in the commercialization of the technology is improving the reaction rates and specific activities of the biocatalysts, such as the bacteria and enzymes that are involved in the desulfurization reactions. The reaction rates and specific activities (sulfur removed/hour/gram of biocatalyst that have been reported in the literature are much lower than those necessary for optimal commercial technology. Therefore, improvements in the longevity and specific activity of the biocatalyst are desirable.

SUMMARY OF THE INVENTION

The invention relates to the discovery that the rate of microbial desulfurization of fossil fuels is enhanced by the addition of a flavoprotein to the biocatalyst. The invention is drawn to a method for enhancing the rate of desulfurizing a fossil fuel containing organic sulfur compounds, comprising the steps of:

a) contacting the fossil fuel with an aqueous phase containing a biocatalyst capable of cleaving carbon-sulfur bonds and a rate-enhancing amount of a flavoprotein, thereby forming a fossil fuel and aqueous phase mixture;

b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase.

The invention also relates to a recombinant microorganism containing one or more recombinant DNA molecules which encode a biocatalyst capable of desulfurizing a fossil fuel containing organic sulfur molecules and which encode a flavoprotein.

The invention also relates to a composition comprising (a) a biocatalyst capable of desulfurizing a fossil fuel containing organic sulfur molecules and (b) a flavoprotein.

DETAILED DESCRIPTION OF THE INVENTION

In the petroleum extraction and refining arts, the term "organic sulfur" is generally understood as referring to organic molecules having a hydrocarbon framework to which one or more sulfur atoms (called heteroatoms) are covalently joined. These sulfur atoms can be joined directly to the hydrocarbon framework, e.g., by one or more carbon-sulfur bonds, or can be present in a substituent joined to the hydrocarbon framework of the molecule, e.g., a sulfonyl group (which contains a carbon-oxygen-sulfur covalent linkage). The general class of organic molecules having one or more sulfur heteroatoms are sometimes referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked to adjacent carbon atoms in the hydrocarbon framework by aromatic carbon-sulfur bonds are referred to as "sulfur-bearing heterocycles". The sulfur that is present in many types of sulfur-bearing heterocycles is referred to as "thiophenic sulfur" in view of the five-membered aromatic ring in which the sulfur heteroatom is present. The simplest such sulfur-bearing heterocycle is thiophene, which has the composition $C_4H_4S$.

Sulfur-bearing heterocycles are known to be stable to conventional desulfurization treatments, such as hydrodesulfurization (HDS). Sulfur-bearing heterocycles can have relatively simple or relatively complex chemical structures. In complex heterocycles, multiple condensed aromatic rings, one or more of which can be heterocyclic, are present. The difficulty of desulfurization increases with the structural complexity of the molecule. That is, refractory behavior is most accentuated in complex sulfur-bearing heterocycles, such as dibenzothiophene (DBT, $C_{12}H_8S$).

DBT is a sulfur-bearing heterocycle that has a condensed, multiple aromatic ring structure in which a five-membered thiophenic ring is flanked by two six-membered benzylic rings. Much of the residual post-HDS organic sulfur in fossil fuel refining intermediates and combustible products is thiophenic sulfur. The majority of this residual thiophenic sulfur is present in DBT and derivatives thereof having one or more alkyl or aryl groups attached to one or more carbon atoms present in one or both flanking benzylic rings. DBT itself is accepted in the relevant arts as a model compound illustrative of the behavior of the class of compounds encompassing DBT and derivatives thereof in reactions involving thiophenic sulfur. Monticello and Finnerty, *Annual Reviews in Microbiology* 39:371–389 (1985) at 372–373. DBT and derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom. Id. Another characteristic of DBT and derivatives thereof is that, following a release of fossil fuel into the environment, these sulfur-bearing heterocycles persist for long periods of time without significant biodegradation. Gundlach et al. *Science* 221:122–129 (1983). Thus, most prevalent naturally occurring microorganisms do not effectively metabolize and break down sulfur-bearing heterocycles.

A fossil fuel that is suitable for desulfurization treatment according to the present invention is one that contains organic sulfur. Such a fossil fuel is referred to as a "substrate fossil fuel". Substrate fossil fuels that are rich in thiophenic sulfur are particularly suitable for desulfurization according to the method described herein. Examples of such substrate fossil fuels include Cerro Negro or Orinoco heavy crude oils; Athabascan tar and other types of bitumen; petroleum refining fractions such as light cycle oil, heavy atmospheric gas oil, and No. 1 diesel oil; and coal-derived liquids manufactured from sources such as Pocahontas #3, Lewis-Stock, Australian Glencoe or Wyodak coal.

Biocatalytic desulfurization (biocatalysis or BDS) is the excision (liberation or removal) of sulfur from organosulfur compounds, including refractory organosulfur compounds such as sulfur-bearing heterocycles, as a result of the selective, oxidative cleavage of carbon-sulfur bonds in said compounds by a biocatalyst. BDS treatment yields the desulfurized combustible hydrocarbon framework of the former refractory organosulfur compound, along with inorganic sulfur substances which can be readily separated from each other by known techniques such as fractional distillation or water extraction. For example, DBT is converted into hydroxybiphenyl when subjected to BDS treatment. BDS is carried out by a biocatalyst comprising one or more non-human organisms (e.g., microorganisms) that functionally express one or more enzymes that direct, singly or in concert with each other, the removal of sulfur from organosulfur compounds, including sulfur-bearing heterocycles, by the selective cleavage of carbon-sulfur bonds in said compounds; one or more enzymes obtained from such microorganisms; or a mixture of such microorganisms and enzymes. Organisms that exhibit biocatalytic activity are referred to herein as being $Dsz^+$. Organisms that lack biocatalytic activity are referred to herein as being $Dsz^-$.

The invention relates to the improved removal of sulfur from fossil fuels containing organic sulfur molecules comprising adding a rate-enhancing amount of a flavoprotein to the biocatalyst capable of desulfurizing the fossil fuel to facilitate or enhance electron transport to the catalytic site.

The biocatalysts capable of desulfurizing fossil fuels employed herein are, generally, known in the art. Included are microorganisms (viable and non-viable, recombinant and non-recombinant) and enzyme preparations.

Several investigators have reported the genetic modification of naturally-occurring bacteria into mutant strains capable of catabolizing DBT. Kilbane, J. J., *Resour. Cons. Recycl.* 3:69–79 (1990), Isbister, J. D., and R. C. Doyle, U.S. Pat. No. 4,562,156 (1985), and Hartdegan, F. J. et al., *Chem. Eng. Progress* 63–67 (1984). For the most part, these mutants desulfurize DBT nonspecifically, and release sulfur in the form of small organic sulfur breakdown products. Thus, a portion of the fuel value of DBT is lost through this microbial action. Isbister and Doyle reported the derivation of a mutant strain of Pseudomonas which appeared to be capable of selectively liberating sulfur from DBT, but did not elucidate the mechanism responsible for this reactivity.

Kilbane has reported the mutagenesis of a mixed bacterial culture, producing one which appeared capable of selectively liberating sulfur from DBT by the oxidative pathway. This culture was composed of bacteria obtained from natural sources such as sewage sludge, petroleum refinery wastewater, garden soil, coal tar-contaminated soil, etc., and maintained in culture under conditions of continuous sulfur deprivation in the presence of DBT. The culture was then exposed to the chemical mutagen 1-methyl-3-nitro-1-nitrosoguanidine. The major catabolic product of DBT metabolism by this mutant culture was hydroxybiphenyl; sulfur was released as inorganic water-soluble sulfate, and the hydrocarbon portion of the molecule remained essentially intact as monohydroxybiphenyl. Kilbane, J. J., *Resour. Cons. Recycl.* 3:69–79 (1990), the teachings of which are incorporated herein by reference.

Kilbane has also isolated a mutant strain of Rhodococcus from this mixed bacterial culture. This mutant, IGTS8 or ATCC No. 53968, is a particularly preferred biocatalyst for use with the instant invention. The isolation and characteristics of this mutant are described in detail in J. J. Kilbane, U.S. Pat. No. 5,104,801, the teachings of which are incorporated herein by reference. This microorganism has been deposited at the American Type Culture Collection (ATCC), 12301 Park Lawn Drive, Rockville, Md., U.S.A. 20852 under the terms of the Budapest Treaty, and has been designated as ATCC Deposit No. 53968. One suitable ATCC No. 53968 biocatalyst preparation is a culture of the living microorganisms, prepared generally as described in U.S. Pat. No. 5,104,801 and mutants or derivatives thereof. Cell-free enzyme preparations obtained from ATCC No. 53968 or mutants thereof generally as described in U.S. Pat. Nos. 5,132,219, and 5,358,870 can also be used. In the instant method for biocatalytic desulfurization (BDS), the ATCC No. 53968 biocatalytic agent is employed in a continuous desulfurization process for the treatment of a petroleum liquid in which HDS-refractory organic sulfur molecules, such as the aromatic sulfur-bearing heterocycles, constitute a significant portion of the total organic sulfur content.

There are at least two possible types of pathways which result in the specific release of sulfur from DBT: oxidative and reductive. Preferably, an oxidative (aerobic) pathway can be followed. Examples of microorganisms that act by this oxidative pathway, preparations of which are suitable for use as the biocatalyst in the present invention include the microbial consortium (a mixture of several microorganisms) disclosed in Kilbane (1990), 3 RESOUR. CONSERV. RECYCL. 69–79, the microorganisms disclosed by Kilbane in U.S. Pat. No. 5,002,888 (issued Mar. 26, 1991), U.S. Pat. No. 5,104,801 (issued Apr. 14, 1992), U.S. Pat. Nos. 5,344, 778, 5,132,219, 5,198,341, 5,356,813, 5,356,801, 5,358,870 [also described in Kilbane (1990), *Biodesulfurization: Future Prospects in Coal Cleaning*, in PROC, 7TH ANN. INT'L. PITTSBURGH COAL CONF. 373–382], and U.S. Pat. No. 5,198,341 (issued Mar. 30, 1993); and by Omori et al. (1992), *Desulfurization of dibenzothiophene by Coryne-* bacterium sp. strain SY1, 58 APPL. ENV. MICROBIOL. (No. 3) 911–915; and Izumi et al., *Applied and Environmental Microbiology* 60:223–226 (1994) all incorporated herein by reference.

Each of the foregoing microorganisms can function as a biocatalyst in the present invention because each produces one or more enzymes (protein biocatalysts) that carry out the specific chemical reaction(s) by which sulfur is excised from refractory organosulfur compounds. Lehninger, PRINCIPLES OF BIOCHEMISTRY (Worth Publishers, Inc., 1982), p. 8–9; cf. Zobell in U.S. Pat. No. 2,641,564 (issued Jun. 9, 1953) and Kern et al. in U.S. Pat. No. 5,094,668 (issued Mar. 10, 1992). Mutational or genetically engineered derivatives of any of the foregoing microorganisms, as exemplified by the U.S. patents listed above, can also be used as the biocatalyst herein, provided that appropriate biocatalytic function is retained.

Additional microorganisms suitable for use as the biocatalyst or biocatalyst source in the desulfurization process now described can be derived from naturally occurring microorganisms by known techniques. As set forth above, these methods involve culturing preparations of microorganisms obtained from natural sources such as sewage sludge, petroleum refinery wastewater, garden soil, or coal tar-contaminated soil under selective culture conditions in which the microorganisms are grown in the presence of refractory organosulfur compounds such as sulfur-bearing heterocycles as the sole sulfur source; exposing the microbial preparation to chemical or physical mutagens; or a combination of these methods. Such techniques are recounted by Isbister and Doyle in U.S. Pat. No. 4,562,156 (issued Dec. 31, 1985); by Kilbane in 3 RESOUR. CONSERV. RECYCL. 69–79 (1990), U.S. Pat. Nos. 5,002,888, 5,104,801 and 5,198,341; and by Omori and coworkers in 58 APPL. ENV. MICROBIOL. (No. 3) 911–915 (1992), all incorporated by reference.

As explained above, enzymes are protein biocatalysts made by living cells. Enzymes promote, direct or facilitate the occurrence of a specific chemical reaction or series of reactions (referred to as a pathway) without themselves becoming consumed as a result thereof. Enzymes can include one or more unmodified or post-translationally or synthetically modified polypeptide chains or fragments or portions thereof, additional coenzymes, cofactors, or coreactants which collectively catalyze the desired reaction or series of reactions. The reaction or series of reactions relevant to the present invention culminates in the excision of sulfur from the hydrocarbon framework of a refractory organosulfur compound, such as a sulfur-bearing heterocycle. The hydrocarbon framework of the former refractory organosulfur compound remains substantially intact. Microorganisms or enzymes employed as biocatalysts in the present invention advantageously do not consume the hydrocarbon framework of the former refractory organosulfur compound as a carbon source for growth. As a result, the fuel value of substrate fossil fuels exposed to BDS treatment does not deteriorate.

Although living microorganisms (e.g., a culture) can be used as the biocatalyst herein, this is not required. Biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells. Kilbane and Monticello disclose enzyme preparations that are suitable for use herein in U.S. Pat. No. 5,132,219 (issued Jul. 21, 1992), and U.S. Pat. No. 5,358,870 (filed Jun. 11, 1992), for example. Rambosek et al. disclose recombinant microorganisms and enzyme preparations, engineered from Rhodococcus sp. ATCC No. 53968 and suitable for use herein, in U.S. Pat. No. 5,356,813. Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the treated fossil fuel which has been depleted of refractory organosulfur compounds.

In the biocatalytic desulfurization stage, the liquid fossil fuel containing sulfur-bearing heterocycles is combined with the biocatalyst and flavoprotein. The relative amounts of biocatalyst and flavoprotein and liquid fossil fuel can be adjusted to suit particular conditions, or to produce a particular level of residual sulfur in the treated, deeply desulfurized fossil fuel. The amount of biocatalyst preparation to be combined with a given quantity of liquid fossil fuel will reflect the nature, concentration and specific activity of the particular biocatalyst used, as well as the nature and relative abundance of inorganic and organic sulfur compounds present in the substrate fossil fuel and the degree of deep desulfurization sought or considered acceptable.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms (e.g., ATCC No. 53968) is used as the biocatalyst preparation, a suitable culture medium lacking a sulfur source other than sulfur-bearing heterocycles can be inoculated with suitable microorganisms and fermented until a desired culture density is reached. The resulting culture can be diluted with additional medium or another suitable buffer, or microbial cells present in the culture can be retrieved e.g., by centrifugation, and resuspended at a greater concentration than that of the original culture. The concentrations of microorganism and enzyme biocatalyst can be adjusted similarly. In this manner, appropriate volumes of biocatalyst preparations having predetermined specific activities and/or concentrations can be obtained.

Flavoproteins which can be employed herein include those generally known in the art. Flavins include flavin mononucleotide (FMN) or flavin adenine dinucleotide (FAD). Flavoproteins include flavin reductase or FMN reductase. Flavoproteins, such as flavin reductase, or more preferably FMN reductase, can be used directly as found in nature (e.g., a microbial fraction which contains the flavoprotein), obtained commercially or can be made recombinantly. For example, the DNA sequence of Vibrio flavin reductase is set forth in Lei et al., *J. Bacter.* 176(12):3552–3558 (1994) and can be used to transform a suitable host microorganism as is known in the art and discussed in U.S. Pat. No. 5,356,801, for example. Alternatively, the flavoprotein can be that endogenous to the desulfurization biocatalyst, such as the cell-free fraction described below.

In another embodiment, the flavoprotein can be overexpressed by the desulfurization microorganism (such as IGTS8). This can be accomplished, for example, by mutagenesis. Suitable mutagens include radiation, e.g., ultraviolet radiation, and chemical mutagens, such as N-methyl-N'-nitrosoguanidine, hydroxylamine, ethylmethane-sulfonate and nitrous acid. The mutagenesis can be conducted according to methods generally known in the art.

Where the flavoprotein is recombinant, the protein can be made in situ, such as by the addition of a recombinant microorganism which contains a DNA sequence which encodes the flavoprotein. In a particularly preferred embodiment, the recombinant microorganism encoding the flavoprotein also possesses the enzymes capable of desulfurizing the fossil fuel. For example, the DNA encoding flavoprotein can be transformed into IGTS8 or another microorganism capable of desulfurizing a fossil fuel. In another example, the DNA encoding the flavoprotein is simultaneously or independently transformed into a common host cell with the DNA encoding the desulfurization biocatalyst. The DNA encoding the flavoprotein can be, for example, under the control of the same or different promoter as the DNA encoding the biocatalyst capable of desulfurizing the fossil fuel. In one embodiment, the flavoprotein DNA is incorporated or ligated into the desulfurization gene cluster or operon of IGTS8.

The flavoprotein is added to the reaction mixture in a rate-enhancing amount. "Rate-enhancing amount," as defined herein, is an amount which will significantly increase the rate of desulfurization of the biocatalyst, as originally obtained. For example, where the biocatalyst is IGTS8, a cell-free fraction or purified enzyme preparation thereof, a "rate-enhancing amount" of flavoprotein is an amount of flavoprotein that, in addition to that inherently present in the biocatalyst as obtained, will significantly increase the rate of desulfurization. The rate of desulfurization can be increased, for example, by at least 25%, 50% or 100% in comparison to the rate employing the biocatalyst per se.

As summarized above, the invention described herein relates in one aspect to a DNA molecule or fragment thereof containing a gene or genes which encode a flavoprotein and/or a biocatalyst capable of desulfurizing a fossil fuel that contains organosulfur compounds. The DNA molecule or fragment thereof can be purified and isolated DNA obtained from, e.g., a natural source, or can be recombinant (heterologous or foreign) DNA that is, e.g., present in a non-human host organism. The following discussion, which is not to be construed as limiting on the invention in any way but is presented for purposes of illustration, recounts the isolation of DNA encoding a desulfurizing biocatalyst from a strain of Rhodococcus sp. ATCC No. 53968, that is known to express suitable biocatalytic activity. This preferred strain of Rhodococcus is disclosed in U.S. Pat. No. 5,104,801 (issued 1992), the teachings of which are incorporated herein by reference, and has been referred to in the literature as IGTS8. Other organisms that are known to express suitable biocatalytic activity and thus are viewed as suitable sources of the DNA of the present invention include the strain of *Bacillus sphaericus* described in U.S. Pat. No. 5,002,888 and deposited with the American Type Culture Collection as ATCC No. 53969 and the Corynebacterium strain described in Omori et al. *Appl. Env. Microbiol.* 58(3):911–915 (1992).

Mutant strains of Rhodococcus that are incapable of cleaving carbon-sulfur bonds ($Dsz^-$), are produced by exposing a strain of Rhodococcus, e.g., ATCC No. 53968, that exhibits biocatalytic activity, to a mutagen under appropriate conditions that are known to or readily ascertainable by those skilled in the art. Suitable mutagens include radiation, e.g., ultraviolet radiation, and chemical mutagens, e.g., N-methyl-N'-nitro-nitrosoguanidine (NTG), hydroxylamine, ethylmethanesulphonate (EMS) and nitrous acid. Mutants thus formed are allowed to grow in an appropriate medium and screened for carbon-sulfur bond cleavage activity. A method of screening which allows for an accurate detection of carbon-sulfur bond cleavage activity is suitable in the method of the present invention. Suitable methods of screening for this activity include exposing the different mutants to carbon-sulfur bond containing molecules (e.g., DBT) and measuring carbon-sulfur bond cleavage. In a preferred embodiment, the mutants are exposed to DBT, such that the breakdown product, hydroxybiphenyl (HBP), which fluoresces under short wave ultraviolet light, is produced. HBP can also be detected calorimetrically through its blue reaction product with Gibbs' reagent. Other methods include gas and liquid chromatography, infrared and nuclear magnetic resonance spectrometry. See Kodama et al. *Applied and Environmental Microbiology*, pp. 911–915 (1992) and Kilbane and Bielaga, Final Report D.O.E. Contract No. DE-AC22-88PC8891 (1991). Once $Dsz^-$ mutants are identified and isolated, clones thereof are propagated using standard techniques and subjected to further analysis.

Concurrent with the mutagenesis of the above-described culture of the $Dsz^+$ organism, Rhodococcus, a second culture of the same $Dsz^+$ organism is maintained in culture. $Dsz^+$ organism DNA is extracted from this culture of Rhodococcus. Various methods of DNA extraction are suitable for isolating the DNA of this organism. Suitable methods include phenol and chloroform extraction. See Maniatis et al. *Molecular Cloning, A Laboratory Manual,* 2d, Cold Spring Harbor Laboratory Press, pg 16.54 (1989), herein referred to as Maniatis et al.

Once the DNA is extracted from Rhodococcus, the DNA is cut into fragments of various kilobase lengths, which upon cloning into a suitable plasmid shuttle vector collectively make up a DNA library. Various methods of fragmenting the DNA of Rhodococcus to purify DNA therefrom, including the DNA of the present invention, can be used, e.g., enzymatic and mechanical methods. Any four-base recognition restriction endonuclease such as TaQI or Sau 3A is suitable for fragmenting the DNA. Suitable methods of fragmenting DNA can be found in Maniatis et al.

The various DNA fragments are inserted into several $Dsz^-$ mutant clones of Rhodococcus, with the purpose of isolating the fragment of DNA that encodes the biocatalyst of the present invention. The transformation of a previously $Dsz^-$ mutant cell to a $Dsz^+$ transformed cell is evidence that the inserted DNA fragment encodes a biocatalyst. Any method of inserting DNA into Rhodococcus which allows for the uptake and expression of said fragment is suitable. In a preferred embodiment, electroporation is used to introduce the DNA fragment into Rhodococcus. See Maniatis et al.

Once transformed, $Dsz^+$ mutant has been produced and identified, DNA fragment encoding the $Dsz^+$ biocatalyst can be identified and isolated. The encoded biocatalyst can then be produced using the isolated DNA in various methods that are well known and readily available to those skilled in the art. In addition, the isolated DNA can be sequenced and replicated by known techniques and/or ligated to DNA encoding a flavoprotein employing, e.g., the techniques described in Maniatis et al.

As noted previously, the above-described method for isolating the DNA of the present invention can be applied to $Dsz^+$ organisms other than Rhodococcus microorganisms, e.g., of the strain ATCC No. 53968. Thus, *Bacillus sphaericus* ATCC No. 53969 or Corynebacterium sp. SY1 can be used as the source organism for the DNA of the present invention. Furthermore, once isolated, the DNA of the present invention can be transformed into a non-human host organism other than a Dsz⁻ mutant of the source organism. Thus, the DNA of the present invention can be transformed into, e.g., a suitable strain of *Escherichia coli* bacteria. Other types of non-human host organism can also be used, including unicellular organisms (e.g., yeast) and cells established in culture from multicellular organisms.

Other methods of isolating the DNA of the present invention, include variations on the rationale described above. For example, fragments of sequences from the IGTS8 gene cluster can be used as hybridization probes to identify similar DNA molecules.

The techniques described herein can also be used to isolate and clone DNA that encodes a flavoprotein, such as the endogenous flavoprotein of IGTS8.

The recombinant DNA molecule or fragment thereof of the present invention is intended to encompass any DNA resulting from the insertion into its chain, by chemical or biological means, of one or more genes encoding a biocatalyst capable of selectively cleaving carbon-sulfur bonds and a flavoprotein, said gene not originally present in that chain. Recombinant DNA includes any DNA synthesized by procedures using restriction nucleases, nucleic acid hybridization, DNA cloning, DNA synthesis or any combination of the preceding. Methods of construction can be found in Maniatis et al., and in other methods known by those skilled in the art.

Procedures for the construction of the DNA plasmids or vectors of the present invention include those described in Maniatis et al. and other methods known by those skilled in the art. The terms "DNA plasmid" and "vector" are intended to encompass any replication competent plasmid or vector capable of having foreign or exogenous DNA inserted into it by chemical or biological means and subsequently, when transformed into an appropriate non-human host organism, of expressing the product of the foreign or exogenous DNA insert (i.e., of expressing the biocatalyst and flavo-protein of the present invention). In addition, the plasmid or vector must be receptive to the insertion of a DNA molecule or fragment thereof containing the gene or genes of the present invention, said gene or genes encoding a biocatalyst that selectively cleaves carbon-sulfur bonds in organosulfur compounds. Procedures for the construction of DNA plasmid vectors include those described in Maniatis et al. and others known by those skilled in the art.

The plasmids of the present invention include any DNA fragment containing a gene or genes encoding a flavoprotein and/or a biocatalyst that selectively cleaves carbon-sulfur bonds in organosulfur compounds. The term "plasmid" is intended to encompass any DNA fragment. The DNA fragment should be transmittable, for example, to a host microorganism by transformation or conjugation. Procedures for the construction or extraction of DNA plasmids include those described in Maniatis et al. and others known by those skilled in the art.

The transformed non-human host organisms of the present invention can be created by various methods by those skilled in the art. For example, electroporation as explained by Maniatis et al. can be used. By the term "non-human host organism" is intended any non-human organism capable of the uptake and expression of foreign, exogenous or recombinant DNA. Preferably, the host organism is a bacterium, more preferably a pseudonomad.

The method of desulfurizing a fossil fuel of the present invention involves two aspects. First, a host organism or biocatalytic preparation obtained therefrom is contacted with a fossil fuel to be desulfurized. This can be done in any appropriate container, optionally fitted with an agitation or mixing device. The mixture is combined thoroughly and allowed to incubate for a sufficient time to allow for cleavage of a significant number of carbon-sulfur bonds in organosulfur compounds, thereby producing a desulfurized fossil fuel. In one embodiment, an aqueous emulsion or microemulsion is produced with an aqueous culture of the organism or enzyme fraction and the fossil fuel, allowing the organism to propagate in the emulsion while the expressed biocatalyst cleaves carbon-sulfur bonds.

Variables such as temperature, mixing rate and rate of desulfurization will vary according to the organism biocatalyst and/or flavoprotein, used. The parameters can be determined through no more than routine experimentation.

Several suitable techniques for monitoring the rate and extent of desulfurization are well-known and readily available to those skilled in the art. Baseline and time course samples can be collected from the incubation mixture, and prepared for a determination of the residual organic sulfur in the fossil fuel. The disappearance of sulfur from organosulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

The process and the biocatalytic compositions (including the recombinant microorganisms) of the claimed invention result in a significant and unexpected improvement over earlier disclosed processes of desulfurization. It has been shown that the use of the flavoprotein can result in an improvement in the rate of reaction in comparison to a system where no additional flavoprotein is added. This is particularly unexpected in view of recent discussions in the literature suggesting that FAD binds directly to DSZC (Denome et al., J. Bacteriol., 176:6707–6716, 1994) and the suggestion that NADH is the only cofactor required for the system (Ohshiro et al., FEMS Microbiol. Lett. 118:341–344, 1994).

Without being limited to any particular mechanism, it is believed that the pathway of the desulfurization reaction is set forth below:

Without being limited to any particular theory, the flavoprotein is believed to be a short electron transport chain to deliver the reducing equivalents from NADH (or other electron donor) to the enzymes, DSZC (or Sox C) and/or DSZA (or Sox A). The enzyme DSZC is believed to be responsible for the biocatalysis of the oxidation reaction of DBT to $DBTO_2$. The enzyme DSZA is believed to be responsible for the reaction of $DBTO_2$ to phenol-phenylsulfite (PPS).

As such, it is particularly preferred to add the cofactor, FMN, to the reaction medium as well as an electron donor, NADH or NADPH. The choice of NADH or NADPH, for example, is dependent upon the flavoprotein selected, as is known in the art. In the examples below, NADPH was employed where the Vibrio flavoprotein was used. Also preferred is the addition of an NADH or NADPH regeneration system for converting $NAD^+$ to NADH, according to methods known in the art.

The invention will now be further illustrated by the way of the following examples.

Exemplification

EXAMPLE 1
FMN Enhances the in Vitro Activity of DSZ Materials and Methods

Fifteen ml of bacteria of IGTS8 grown in a basal salts medium at 30° C. to an $A_{600}$ of about 10 were collected by centrifugation and resuspended in 4 ml of 0.1 M sodium phosphate buffer at pH 7.5. The cells were lysed by two passes through a French pressure cell at 17,000 psi. The detergent CHAPS was added to the cell lysate to 0.1% final concentration. This mixture was then placed on ice for 15 minutes and centrifuged at 15,000×g for 15 minutes. The supernatant fraction was used in cell free enzyme assays.

Enzyme reaction mixtures contain all or some of the following components: 1.0 mM DBT, 3.2 mM NADH, 1% lecithin (to increase to solubility of DBT in this aqueous mixture) 5 μM FAD or FMN and the cell protein extract described above in concentrations ranging from 0.1–1.0 mg/ml. The total reaction volume was 0.6 ml and the reactions were incubated at 30° C. with shaking for 1 hour before being stopped by addition of 1 ml of acetonitrile. The mixture was then centrifuged and a portion of the supernatant analyzed by HPLC for 2-HBP concentration against known standards. Protein concentration was determined by the protein assay kit from Biorad (Hercules, Calif.).

Results

As shown by Ohshiro et al. (*FEMS Microbiol. Lett.* 18:341–344 (1994)) the conversion of DBT to 2-HBP is dependent upon the addition of reducing equivalents in the form of NADH to an in vitro reaction mixture (Table 1). These authors, however, reported that no other cofactor was active in this reaction.

TABLE 1

Requirement of flavin mononucleotide (FMN) DBT desulfurization by IGTS8

| Chemicals Added | DBT sulfoxide (ug) | DBT sulfone (ug) | 2-HBP (ug) |
|---|---|---|---|
| NADH[a] | 0 | 0 | 17.0 |
| NADH | 0 | 0.4 | 0 |
| NADH + FAD | 0 | 0 | 0 |
| FMN | 0 | 0 | 0 |
| NADH + FMN | 0 | 0 | 2.5 |

[a]The reaction conditions are as discussed above except that the protein concentration was 1.6 mg/ml.

If a crude protein extract of IGTS8 prepared as above, is diluted to about 0.16 mg/ml protein concentration the extract loses its ability to produce 2-HBP from DBT in the presence of NADH alone. In this case, the addition of FMN (flavin mononucleotide) to the reaction mixture restores this ability. The addition of FAD (flavin adenine dinucleotide) has no effect (Table 1). Dialysis of the extract has the same effect (loss of desulfurization activity and with restoration by the addition of FMN and NADH). These results show that both NADH and FMN participate in desulfurization and that they must be present together in order for the reaction to proceed.

EXAMPLE 2
A Purified Heterologous NADPH Dependent FMN Reductase Enhances the Dsz Activity of IGTS8 Extracts The results of experiments described in Example 1 suggest the participation of a flavin (such as, FMN) containing reductase in the desulfurization of DBT catalyzed by IGTS8. In order to test this hypothesis we did the DBT→2-HBP reaction in the presence of a purified heterologous FMN reductase.

Materials and Methods

A crude protein lysate of IGTS8 cells was prepared essentially as described in Example 1. The concentration of protein in this extract was 12.7 mg/ml. In order to measure the desulfurizing activity of this extract, 67 $\mu$M DBT and 5 mM NADPH were added to 300 ul of it along with varying amounts of an NADPH dependent FMN reductase purified from Vibrio harveyi (Lei, et al., Supra). One unit of the reductase as used here will catalyze the reduction of 1 $\mu$mole of FMN per minute using NADPH as substrate.

Results

Figure 1:
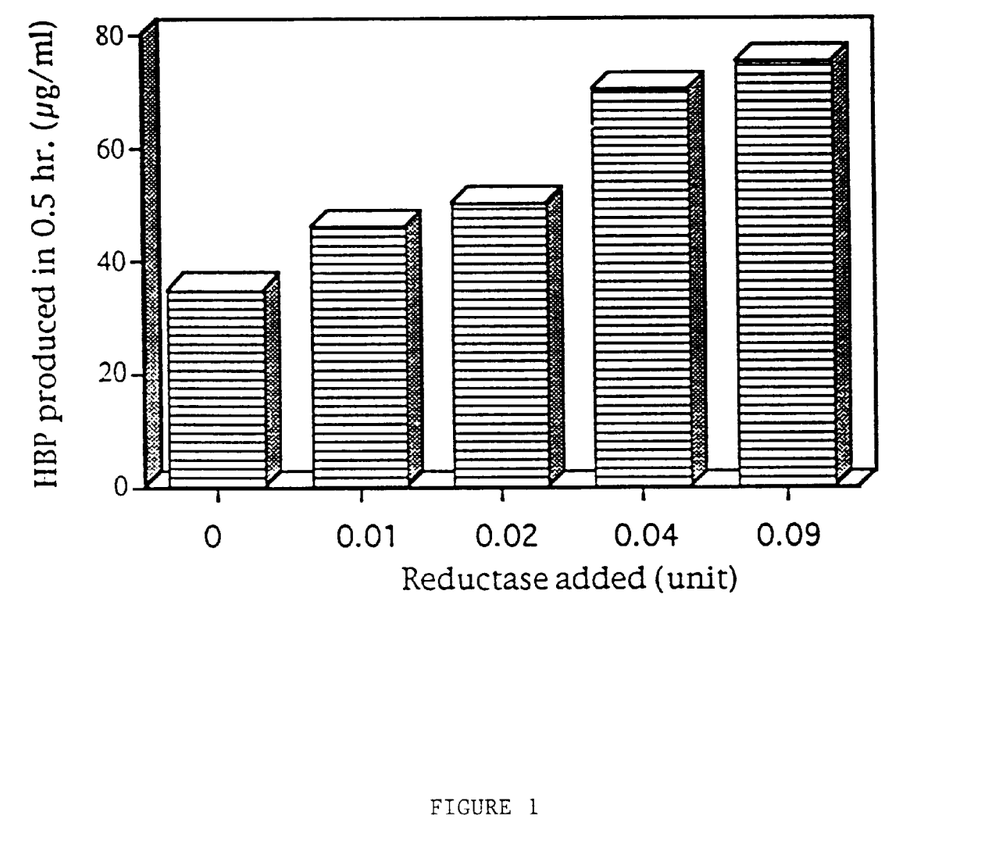
FIG. 1 is a graphic illustration of the conversion of DBT to 2-HBP by an extract of Rhodococcus sp. ATCC 53968, IGTS8, upon the addition of flavoprotein.

When 0 to 0.090 units of the V. harveyi reductase are added to a 300 ul reaction mixture as described above, there is a very strong stimulation of desulfurization activity by the reductase. The addition of 0.09 units increase the activity more than two-fold (FIG. 1). These results show that in the desulfurization reaction described here, the overall potential of the extract to catalyze the reaction is substantially improved by the addition of a flavin containing reductase.

EXAMPLE 3
Expression of the Dsz Phenotype in E. coli is Dependent on FRP

Materials and Methods

Construction of dsz expression Vector pEX16

Figure 2:
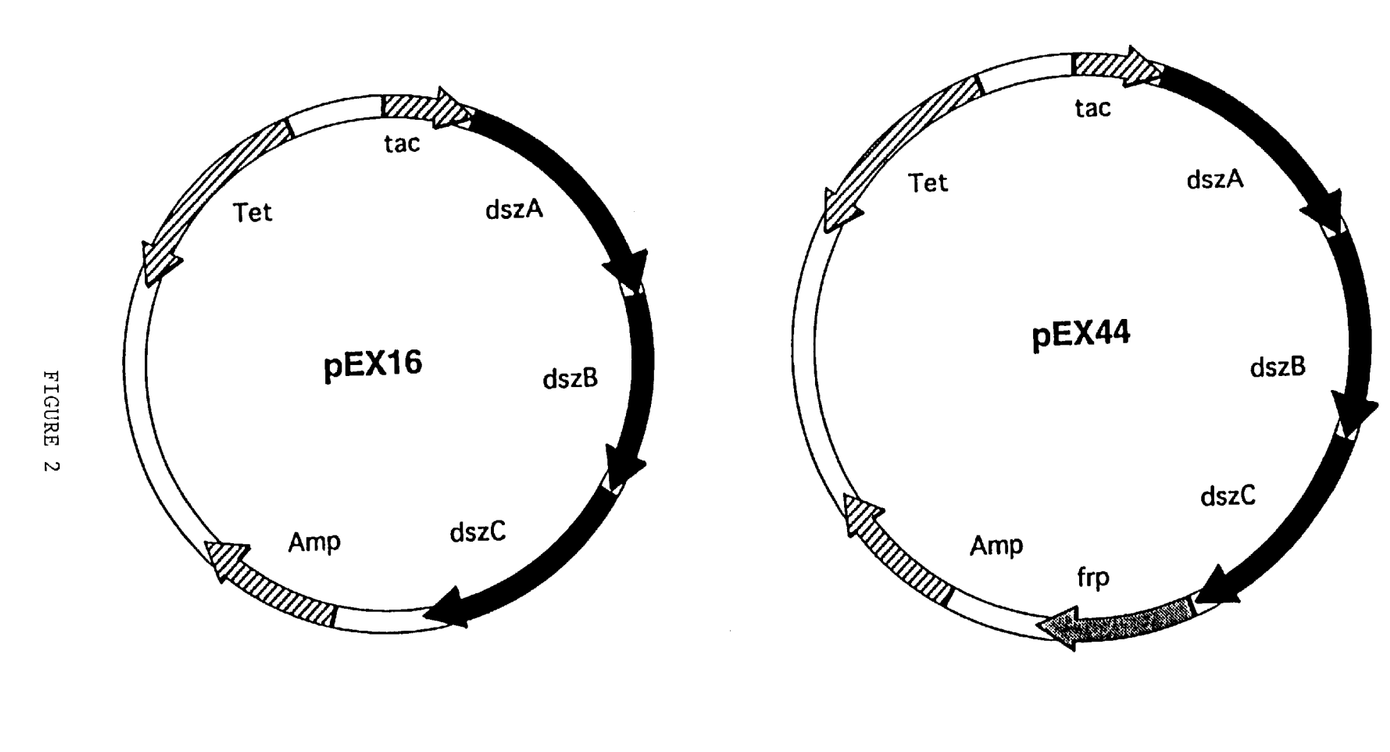
FIG. 2 is a graphic illustration of plasmids, pEX16 and pEX44, wherein the desulfurization gene cluster are presented alone or with the flavoprotein gene, frp, ligated directly to the dsz genes and becoming a part of the dsz gene cluster.

Plasmid pEX16 contains the dszABC genes under transcriptional control of the tac promoter sequence of E. coli. This plasmid was constructed through the following steps: the synthetic duplex DNA oligonitcleotide adaptor sequence riology 176:3552–3558 (1994)) was added to plasmid pEX16 using the following steps. Plasmid pFRPI (Lei, et al. (1994)) was digested with restriction endonuclease Earl and the ends made blunt with dNTP and DNA polymerase large fragment (Klenow). A double stranded SpeI linker fragment (N.E. Biolabs) was added to these blunt ends by ligation; followed by digestion with SpeI. Plasmid pEX16 was then digested at a unique SpeI site lying at the 3' end of the dszABC gene cluster and ligated with the SpeI-ended frp gene fragment. The resulting clone containing the dszABC and frp genes under control of the tac promoter is called pEX44 (FIG. 2).

Preparation of Cell Lysate and Assay of Dsz Activity in Extracts of E. coli Harboring pEX16 or pEX44

Cultures of E. coli cells (50 ml) that had been grown at 37° C. in YT medium were induced for cloned gene expression by the addition of 0.1 mM IPTG (final concentration). The cells were collected by centrifugation resuspended in 0.1M phosphate buffer (pH 7.5) and lysed by 2 passages through a french pressure cell at 17,000 psi. The lysate was centrifuged at 15,000×g for 15 minutes and the supernatant fraction retained for enzyme assay. The reaction mixture contained 0.1 M phosphate buffer, 5 $\mu$M FMN, 0.67 mM DBT, 3 mM NADPH, protein extract (12 mg/ml) with a final volume of 300 ul.

Results

Growth of E. coli on DBT as a Sole Sulfur Source is Dependent on DSZABC and frp

IGTS8 will grow on DBT as a sole sulfur source. Wild type strains of Escherichia coli will not. Furthermore, when a strain of E. coli harboring plasmid pEX16, expressing the dszABC genes is placed in defined growth medium containing DBT as the sole source of sulfur, it will not grow despite strong expression of all three gene products. However, the same strain of E. coli harboring plasmid pEX44, expressing dszABC and frp will grow under these conditions. These results show that heterologous expression of the Dsz phenotype is significantly enhanced by a flavoreductase protein.

Figure 3:
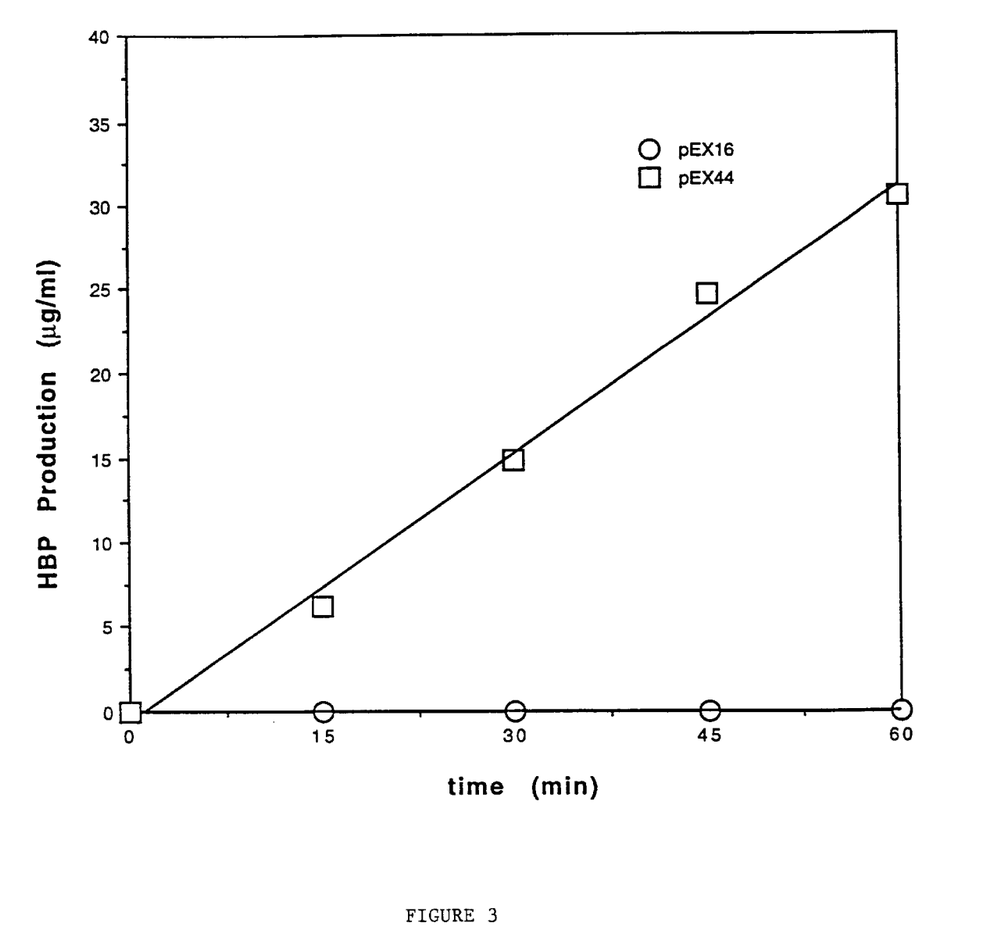
FIG. 3 is a graphic illustration depicting the increase in the rate of desulfurization of DBT when a plasmid co-expressing a flavoprotein is employed.

Extracts of E. coli strains containing either plasmid pEX16 or pEX44 were prepared and assayed for conversion of DBT to 2-HBP as described above. The results shown in FIG. 3 are obtained establishing that conversion is enhanced was ligated into plasmid pUC19 (Yanisch-Perron et al., Gene 33 :103–119 (1985)) that had been digested with endonucleases EcoRI and Hind III, resulting in plasmid pEX13. pEX13 was then digested with endonucleases NsiI and BsiwI. A 4.5 kb NsiI/BsiwI restriction fragment from plasmid pTOXil (U.S. Pat. No. 5,356,801) containing the dszABC structural genes was then isolated and ligated to the digested pEX13 DNA, resulting in plasmid pEX14. A mixture of a 4.5 kbp BglII/SpeI fragment from pEX14 and BAMH1/SpeI cut plasmid pT3XI-2 (Hale, K, a pKK223-3 (Pharmacia) derivative containing a tetracycline resistance gene and a tac promoter) were ligated such that the tac promoter was oriented to direct transcription of dszABC. This plasmid is called pEX16. (FIG. 2)

Construction of a Plasmid Coding DSZABC and frp

A 0.9 kbp Fragment of DNA Containing the frp (flavoreductase) gene of Vibrio harveyi (Lei et al. J. Bacteby the presence in the extract of the expression product of the frp gene, NADPH dependent FMN reductase.

EXAMPLE 4
Isolation of Endogenous Flavoprotein of IGTS8 Methods and Materials Bacterial Strains and Growth IGTS8 was grown until early stationary phase in BSM/Hunters medium (Denome et al., Applied and Environmental Microbiology 59 (9 (:2837–2843 (1993)) by shaking at 250 rpm at 30° C. (typically about 85 hours).

E. coli MZ1 containing the plasmid pSAD267-1 encoding DSZA (Denome et al., J. Bact. 176:6707–6716 (1994)) was grown in BSM/Hunters medium supplemented with 0.4 mg mL$^{-1}$ biotin, 50 mg mL$^{-1}$ each of histidine, isoleucine and valine, 100 $\mu$g mL$^{-1}$ ampicillin and 1.5 mM Na$_2$SO$_4$. A single colony from a fresh agar plate was used to inoculate 50 mL liquid culture which was shaken (250 rpm) overnight at 30° C. A 10 mL aliquot of this culture was used to inoculate 500 mL of the same medium and grown to an $OD_{600}$ of approximately 0.4. At this point the expression of DSZA was induced by increasing the temperature to 39° C. for 2 hours then returned to 30° C. until an $OD_{600}$ of approximately 3 was reached. Typically 3 L of cell culture was used for purification.

E. coli MZ1 containing the plasmid pSAD269-2A encoding DSZC (Denome et al. (1994)) was grown in LB medium supplemented with 100 μg $mL^{-1}$ ampicillin as described above for MZ1:: pSAD267-1.

Column Chromatography

All chromatography steps were carried out at 4° C. or on ice. IGTS8 cells, harvested by centrifugation, were washed once with 25 mM EPPS pH 8 (buffer A) containing 1 mM EDTA and 1 mM DTT and resuspended in 25 mM EPPS pH 8, 1 mM EDTA, 1 mM DTT, 100 mM NaCl, 10 mM $MgCl_2$ and 0.15 mM PMSF. DNase and RNase were added as solids. The cells were ruptured in an Aminco French pressure cell at 40,000 psi. The cell suspension was passed through the French press twice and then centrifuged at 39,800×g for 30 minutes at 4° C. The pellet (consisting of unbroken cells and cell debris) was discarded while the supernatant was loaded on a Pharmacia Q-Sepharose Fast Flow column (2.6 cm×14 cm) equilibrated with buffer A containing 5% buffer B (buffer A+2 M NaCl) at a flow rate of 2 mL $min^{-1}$. The column was washed extensively with the same buffer at a flow rate of 5 mL $min^{-1}$ until the $OD_{280}$ of the eluate was close to 0 and developed with a linear gradient from 5% to 30% buffer B (corresponding to 100 mM to 600 mM NaCl) over 180 minutes. At approximately 240 mM NaCl several yellowish fractions eluted which displayed NADH:DCPIP oxidoreductase activity.

Purification of DSZA from E. coli was accomplished as follows. E. coli cells grown as described above were harvested by centrifugation at 6,000 rpm for 10 minutes and washed twice in buffer A. The cells were resuspended in the same buffer (volume equal to the wet weight of the cells) including 100 mM NaCl, 10 mM $MgCl_2$, 0.15 mM PMSF and DNase and RNase and then ruptured in a French pressure cell at 20,000 psi. The lysate was centrifuged at 39,800×g for 30 minutes to remove unbroken cells and cell debris. The supernatant was loaded on a Pharmacia Q-sepharose Fast Flow column (2.6 cm×14 cm) at a flow rate of 1 mL $min^{-1}$. The column was washed with 5% buffer B until the $OD_{280}$ of the eluent was close to baseline and developed with a linear gradient of 5% to 25% buffer B over 120 minutes at a flow rate of 5 mL $min^{-1}$. The fractions which contained DSZA (as determined by SDS-PAGE) were pooled and dialyzed overnight vs. buffer A at 4° C. The dialysate was loaded onto a Pharmacia Blue Sepharose-6 Fast Flow column connected in line with a Pharmacia Resource Q column equilibrated with buffer A. After a stable baseline had been achieved the Blue Sepharose column was disconnected and the Resource Q column was developed with a linear gradient from 2.5% to 25% buffer B for 60 minutes at a flow rate of 3 mL $min^{-1}$. The fractions containing DSZA (as judged by SDS-PAGE) were pooled, glycerol was added to 10% (w/v) and stored at −20° C. This procedure results in DSZA being 95% pure.

DSZC was purified as follows. Buffer A in this instance was 10 mM BES pH 7.09 containing 1 mM EDTA. The cells were lysed by treatment with 4 mg $mL^{-1}$ lysozyme at room temperature for 1.5 hours. The lysis buffer included 75 mM NaCl, 1 mM DTT and 0.1 mg $mL^{-1}$ PMSF. After lysis was completed $MgCl_2$ was added to 5 mM and DNase and RNase were also added. The supernatant was first centrifuged at 6,000 rpm for 15 minutes, the pellet was discarded and the supernatant was centrifuged again at 39000×g for 1.5 hours. Subsequently the supernatant was loaded onto a Pharmacia Resource Q column equilibrated with buffer A plus 3% buffer B (buffer A with 2 M NaCl) and washed with ten column volumes of the same buffer. The column was developed with a linear gradient from 60 mM NaCl to 500 mM NaCl (3 to 25% buffer B) for 23 minutes at a flow rate of 3 mL $min^{-1}$. Fractions containing DSZC (as determined by SDS-PAGE), eluting around 350 mM NaCl, were pooled and concentrated using Amicon Centriprep 30 (MWCO 30 kDa) to approximately 0.7 mL. 0.25 mL of the concentrated fractions were further chromatographed on a Pharmacia Superose 12 gel filtration column (flow rate of 0.3 mL $min^{-1}$) using 10 mM BES pH 7 as the mobile phase. Fractions containing DSZC were pooled and then lyophilized and stored at −20° C.

Enzyme Assays

NADH dependent DCPIP reduction was assayed as follows. The reaction mixture (1 mL in a d=1 cm cuvette) contained 100 nmol DCPIP and 50 nmol FMN in 25 mM EPPS buffer, pH 8. Reduction of DCPIP is correlated with the loss of absorbance at 600 nm. The absorbance of the stirred mixture was monitored at 600 nm in a Beckman 7500 diode array spectrophotometer. After approximately 30 s 300 nmol NADH was added and it was observed that there was a residual amount of non-enzymatic reduction of DCPIP. After approximately another 30 s the reaction was initiated by the injection of between 1 and 10 μL of the sample to be tested. Enzymatic activity was expressed in either $-OD_{600}$ $min^{-1}$ or μM DCPIP reduced $min^{-1}$ (using $\epsilon_{600}$ =21 $mM^{-1}$ $cm^{-1}$) NADH dependent cyt c reduction was assayed in a similar manner except that absorbance was monitored at 550 nm and the mixture contained 50 nmol cyt c instead of DCPIP. Reduction of ferricytochrome c to ferrocytochrome c is correlated to the increase of absorbance at 550 nm.

Conversion of DBT to DBTO, $DBTO_2$ and HBP, and DBT-sultone to BHBP was assayed by HPLC as described previously using a Synchropak RP C18 reverse phase column (100×4.6 mm) with $H_2O$:acetonitrile of 1. The reaction mixtures, in 100 mM $NaP_i$ pH 7.5, contained in 1 mL, 3 μmol NAD(P)H, 25 nmol FMN (or FAD), crude lysate or purified DSZC (A) and 100 nmol substrate. At time points (every 10 min) 100 μL was removed, added to 100 μL acetonitrile to quench the reaction and analyzed for substrate and product.

Results

Identification of a Flavin Containing Reductase in IGTS8

Figure 4:
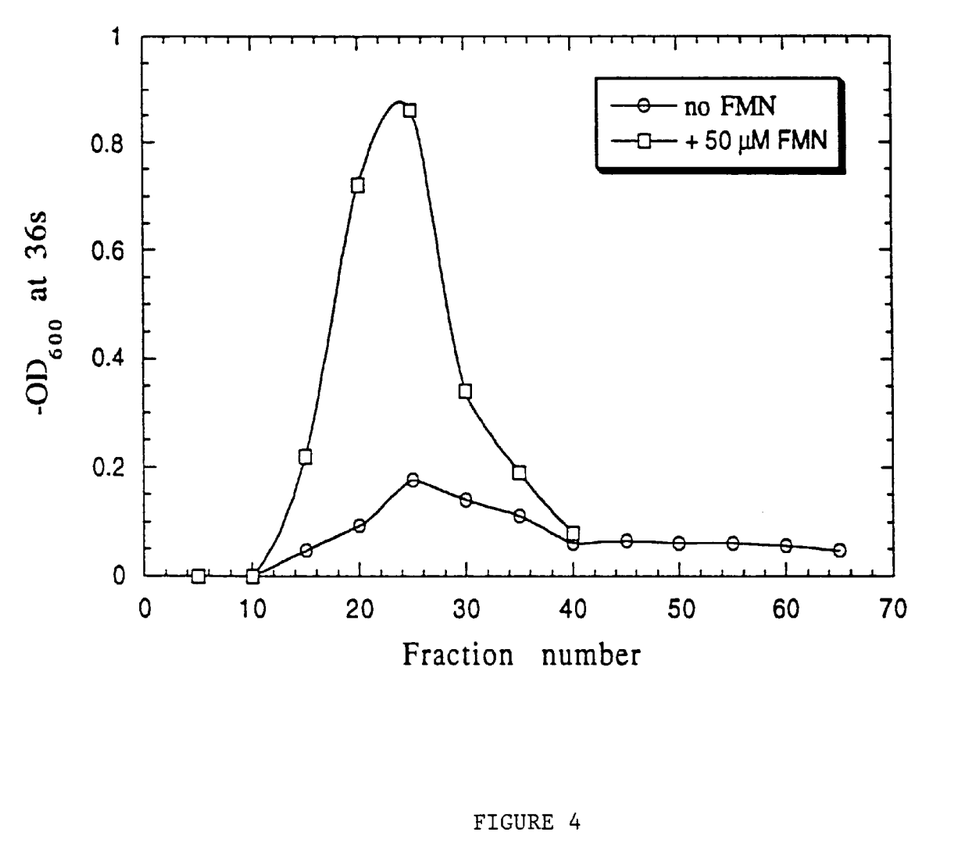
FIG. 4 is a graphic illustration of the elution profile of an endogenous flavoprotein from ATCC 53968.

After separation of IGTS8 crude lysate by anion exchange chromatography it was possible to distinguish several clearly pigmented (yellowish and brownish) fractions. As can be seen in FIG. 4 DCPIP reduction by NADH occurs in several of these fractions with a peak centered around number 25 (approximately 240 mM NaCl). These fractions typically have a slight yellowish tint to them indicating that they contain a flavoprotein. In order to obtain full oxidoreductase activity exogenous flavin must be added to the reaction mixture indicating that during the isolation procedure the endogenous flavin had been lost. The addition of flavin (in this case FMN) enhances both the rate and extent of DCPIP reduction. These fractions also catalyze the reduction of cyt c coupled to the oxidation of NADH.

Activation of DSZA and C by the Flavoprotein Reductase

Figure 5:
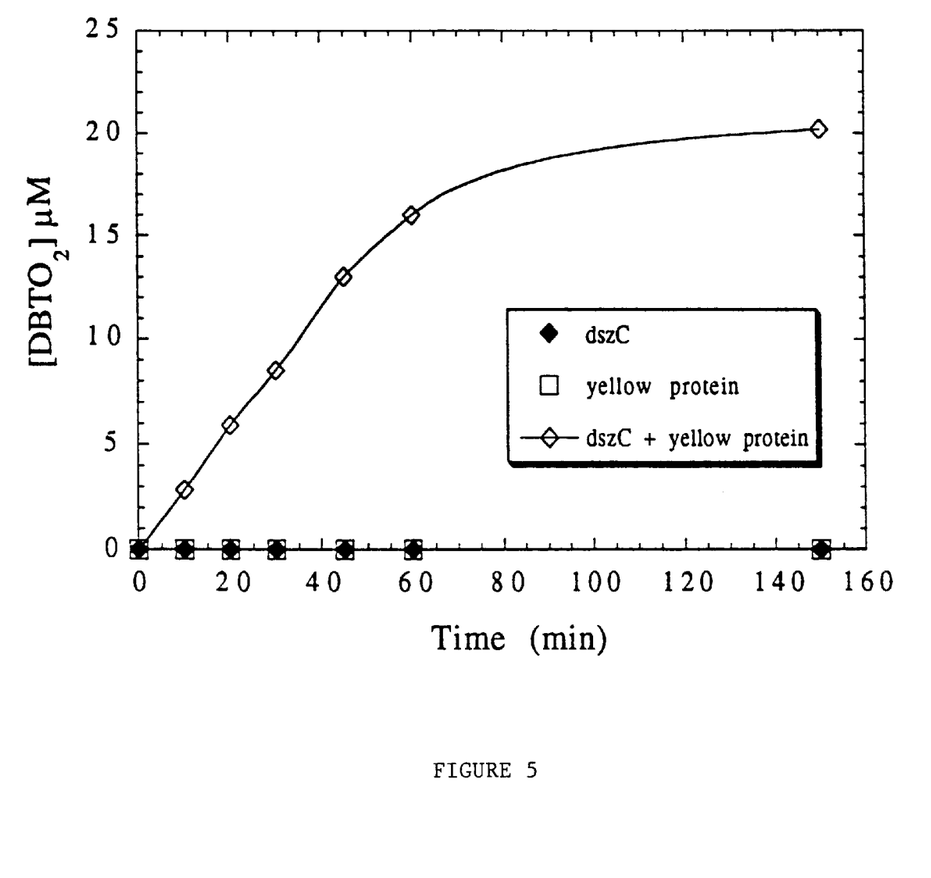
FIGS. 5 and 6 are graphic illustrations depicting the increase in the rate of desulfurization of DBT and DBT-sultone when the fraction containing the endogenous flavoprotein of IGTS8 is added to the DSZ enzyme preparations isolated from E. coli harboring the dsz genes.
Figure 6:
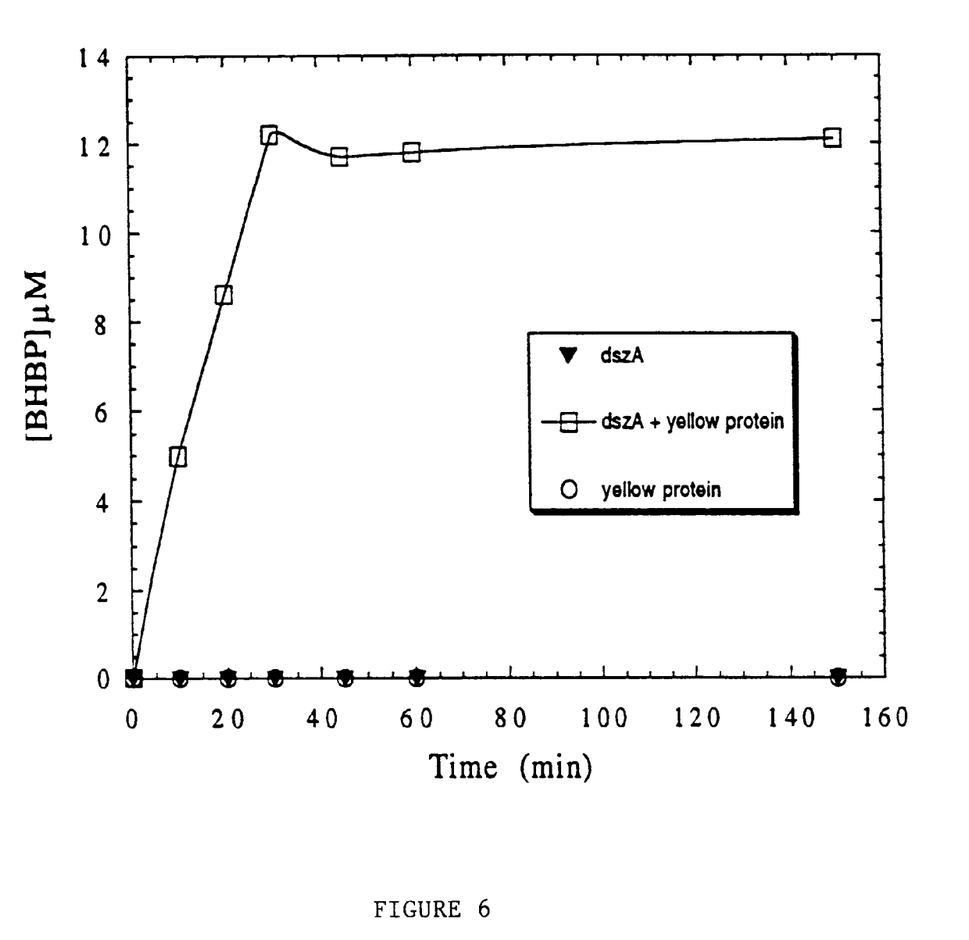

When either DSZA or C is purified from E. coli neither catalyze their respective reactions in a typical one hour assay. FIG. 5 shows that when the flavoprotein oxidoreductase from the yellow fractions is combined with purified *E. coli* DSZA in the presence of both FMN and NADH complete conversion of DBT-sultone to BHBP occurs. The same pattern is observed (FIG. 6) when the yellow fraction is combined with DSZC, FMN and NADH (except here the substrate was DBT and the product $DBTO_2$). These data would suggest that in order for desulfurization to occur, not only must the DSZA, B and C proteins be present, at least a third protein must be included in the pathway which uses flavin as a cofactor and is responsible for oxidizing NADH.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

a) contacting the fossil fuel with an aqueous phase containing a biocatalyst which oxidatively cleaves carbon-sulfur bonds and an amount of a flavoprotein which is sufficient to enhance the rate of biodesulfurization by at least about 25% in comparison to the rate employing the biocatalyst alone, thereby forming a fossil fuel and aqueous phase mixture;

b) maintaining the mixture of step a) under conditions sufficient for cleavage of the carbon-sulfur bonds of the organic sulfur compounds by the biocatalyst, thereby resulting in a fossil fuel having a reduced organic sulfur content; and c) separating the fossil fuel having a reduced sulfur content from the resulting aqueous phase.

2. The method of claim 1 wherein the flavoprotein is flavin reductase.

3. The method of claim 1 wherein the flavoprotein is FMN reductase.

4. The method of claim 3 further comprising adding NADH or NADPH.

5. The method of claim 4 wherein the fossil fuel is a liquid hydrocarbon.

6. The method of claim 4 wherein the fossil fuel is a liquified hydrocarbon.

What is claimed is:

1. A method for enhancing the rate of biodesulfurization of a fossil fuel containing organic sulfur compounds, comprising the steps of:

7. The method of claim 4 wherein the biocatalyst capable of cleaving carbon-sulfur bonds and FMN reductase are immobilized.

8. The method of claim 4 wherein the cleavage of the carbon-sulfur bonds is performed by an oxidative pathway.

9. The method of claim 8 wherein the biocatalyst capable of cleaving carbon-sulfur bonds is a microorganism.

10. The method of claim 8 wherein the microorganism contains a recombinant DNA molecule which encodes one or more enzymes capable of cleaving carbon-sulfur bonds.

11. The method of claim 10 wherein the recombinant DNA molecule is derived from Rhodococcus sp. ATCC 53968.

12. The method of claim 8 wherein the biocatalyst capable of cleaving carbon-sulfur bonds is a cell-free fraction.

13. The method of claim 12 wherein the biocatalyst is a cell-free fraction of Rhodococcus sp. ATCC 53968.

14. The method of claim 8 wherein the biocatalyst comprises one or more enzymes or enzyme fractions derived from a microorganism having the capability of cleaving carbon-sulfur bonds.

15. The method of claim 14 wherein the microorganism is Rhodococcus sp. ATCC 53968.

16. The method of claim 2 wherein the flavoprotein is recombinant flavin reductase.

17. The method of claim 16 wherein the biocatalyst capable of cleaving carbon sulfur bonds and recombinant flavin reductase are produced by a single microorganism.

* * * * *